US00PP34695P2

(12) United States Plant Patent
Shoup

(10) Patent No.: US PP34,695 P2
(45) Date of Patent: Nov. 1, 2022

(54) SHRUB ROSE PLANT NAMED 'WICKED SISTER'

(50) Latin Name: *Rosa hybrida*
Varietal Denomination: 'Wicked Sister'

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 0 days.

(21) Appl. No.: 17/490,661

(22) Filed: Sep. 30, 2021

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

*Primary Examiner* — Susan McCormick Ewoldt

(57) ABSTRACT

A new and distinct variety of shrub rose plant, referred to by its cultivar name, 'Wicked Sister', is provided which abundantly, and continuously forms large clusters of pink colored blooms in the form of full-petalled rosettes. The growth habit is upright and arching. The foliage is disease resistant, smooth, and has a slightly waxy finish. The plant propagates from cuttings easily, stably, and uniformly. The new variety is well suited for growing as a heat tolerant and carefree specimen, and as a source of attractive ornamentation and fragrance in the landscape.

1 Drawing Sheet

Latin name: *Rosa hybrida.*
Varietal denomination: 'Wicked Sister'.

SUMMARY OF THE INVENTION

The new variety of *Rosa hybrida* shrub rose plant was created at Brenham, Tex., U.S.A., by artificial pollination wherein two parents were crossed which previously had been observed in the hope that each would contribute their desired traits. The female parent (i.e., the seed parent) was the 'KORtrameilo' variety (U.S. Plant Pat. No. 24,196). The male parent (i.e., the pollen parent) was the 'Auscot' variety (U.S. Plant Pat. No. 7,215). The parentage of the new variety can be summarized as follows:

'KORtrameilo' x 'Auscot'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new shrub rose plant of the present invention possesses the following combination of characteristics:

(a) abundantly, and continuously forms large clusters of pink colored blooms in the form of full-petalled rosettes,
(b) exhibits an upright and arching growth habit,
(c) exhibits exceptional heat tolerance,
(d) forms disease resistant foliage with a smooth and slightly waxy finish,
(e) is well suited for growing as a heat tolerant and carefree specimen, and as a source of attractive ornamentation and fragrance in the landscape.

The new rose can be readily distinguished from its ancestors upon inspecting the blossoms. More specifically, the 'Wicked Sister' variety forms dissimilar pink blossoms when compared with the parental variety 'KORtrameilo' which forms dissimilar red blossoms. Additionally, the new variety exhibits above average heat tolerance as blooms do not reduce in size, when temperatures are in excess of 100° F., as compared to parental variety 'Auscot' which does reduce in size under the aforementioned conditions. Also, 'Auscot' has fewer petals, 70 count, as compared to 'Wicked Sister' of 166 petals and has a larger flower diameter (10 cm) than 'Wicked Sister' of 7 cm.

The new variety of the present invention also can be readily distinguished from other shrub rose plants, including the 'Ausglisten' variety (U.S. Plant Pat. No. 8,671) upon inspection of the petals. For example, the 'Ausglisten' variety forms dissimilar petals with an obtuse apex.

Asexual reproduction of 'Wicked Sister' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Wicked Sister' remain stable, uniform, and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, 'Wicked Sister'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V (2007). The description is based one year old specimens of the new variety during August while growing outdoors on their own roots at Brenham, Tex., U.S.A.

Class: Shrub Rose. Cultivar 'Wicked Sister'.

Plant:

*Height*.—Approximately 0.75 in on average at maturity.

*Width*.—Approximately 0.75 m on average at maturity.

*Habit*.—Uptight and arching.

Stems:

*Size*.—Approximately 72 cm tall by 1.2 cm in caliper.

*Color*.—Immature: 146A. Mature: 144A.

*Prickles*.—Size: Approximately 0.5 cm in length on average. Quantity: Approximately 5 prickles per every 15 cm section of stem. Color: N77A. Shape: Declining. Density: Slightly below average.

*Texture*.—Smooth.

*Internodal spacing*.—Approximately 9.5 cm on average.

Leaves:

*Arrangement*.—Alternate, odd-pinnate, and compound.

*Margin*.—Nearly entire.

*Stipules*.—Size: Approximately 1.1 cm×0.5 cm on average. Margin: Adnate, entire, undulate, and gland-ciliate. Color: 144A. Texture: Waxy.

*Size*.—Approximately 10 cm×7.75 cm on average,

*Petioles*.—Color upper surface: 144A. Color under surface: 140A. Size: Approximately 4.5 cm in length and 1 mm in width on average. Shape: Filiform.

*Glossiness of the upper side of the leaf*.—Strong.

*Rachis*.—Color: 140A.

*Leaflets*.—Number: 5 and 7. Shape: Ovate. Size: Approximately 3.75 cm×2.5 cm on average. Venation: Reticulate. Venation Color: 144A. Apex: Subacuminate. Base: Subacuminate Undulation of Margin: Medium. Texture Upper Surface: Smooth, slightly waxy. Texture Under Surface: Matte. Overall Appearance: :Medium-green and reflexed. Color (Young Foliage) Upper Surface: 172A. Color (Young Foliage) Under Surface: 172A. Color (Adult Foliage) Upper Surface: 146A. Color (Adult Foliage) Under Surface: 146C.

Inflorescence:

*Average size of inflorescence*.—Approximately 15 cm by 12 cm on average.

*Number of flowers per inflorescence*.—Approximately 3 to 5 on average.

*Florescence type*.—Flat, pompom.

*Peduncle*.—Color: 144A. Length: Approximately 4.5 cm on average. Diameter: Approximately 2.5 mm on average. Texture: Glabrous.

*Sepals*.—Number: 5. Size: Approximately 2 cm×0.8 cm on average. Arrangement: Pentamerous and imbricate. Shape: Obcuneate. Margin: Sublaciniate. Sepal Extensions: Very weak. Apex: Acute. Base: Truncate. Texture: Glabrous. Color Upper Surface: 144A. Color Under Surface: 144A.

*Buds*.—Shape: Globose. Size: Approximately 1.5 cm in length and 1.3 cm in width on average. Color (When Opening) Inner Surface: 63A. Color (When Opening) Outer Surface: 61A.

Flower:

*Form*.—Very full rosette.

*Shape*.—Flattened.

*Profile of the lower part of flower*.—Concave.

*Size*.—On average, diameter approximately 7 cm and depth of flower is 1.3 cm.

*Color*.—(When Opening) Upper Surface: 58B. (When Opening) Under Surface: 59B. (When Blooming) Upper Surface: 58B. (When Blooming) Under Surface: 59B. (End Of Blooming) Upper Surface: 58D. (End Of Blooming) Under Surface: 61D.

*Fragrance*.—Sweet, citrusy and candy-like.

*Petal form*.—Suborbicular on outer petals and elliptic-lanceolate on the inner petals.

*Petals*.—Size: Approximately 3.25 cm×2.5 cm on average. Margins: Entire. Shape: Obcordate. Apex: Acute. Base: Acute. Texture: Smooth. Basal Spot: Absent. Number: Approximately 166 on average. Petal Drop: Easily and cleanly after blooming.

*Stamen number*.—Approximately 15 on average.

*Anther color*.—5C.

*Anther shape*.—Obtuse.

*Anther length*.—Approximately 1.5 mm on average.

*Filament color*.—6B.

*Filament length*.—Approximately 4 mm on average.

*Pollen quantity*. Sparse.

*Pollen color*.—6A.

*Pistil form*.—Free and exerted.

*Pistil number*.—Approximately 130 on average.

*Stigma color*.—3C.

*Style color*.—3D.

*Style length*.—Approximately 1 cm on average.

*Receptacle*.—Turbinate. Achenes form on the inside of the fruit. Size: Approximately 1.5 cm×1.5 cm on average when mature.

*Rate of flower opening*.—Average of 2 to 3 days.

*Lasting quality*.—On plant: Approximately 3 to 4 days on average. In vase: Unknown.

Development:

*Vegetation*.—Sturdy and dense.

*Growth rate*.—Average rate of growth.

*Hip/seed formation*.—None unless manually pollinated

Root system:

*Root color*.—19D.

*Root habit*.—Well rounded and fiberous.

Physiology:

*Disease resistance*.—Above average resistance to black spot *Diplocarpon rosae*, downy mildew *Peronospora sparsa*, powdery mildew *Podosphaera pannosa*, and *Cercospora* leaf spot *Cercospora rosicola*.

*Cold hardiness*.—The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zones 6 and 7.

*Heat tolerance*.—The new variety exhibits above average heat tolerance, as blooms do not reduce in size, when temperatures are in excess of 100° F., as compared to parental variety 'Auscot' which does reduce in size under the aforementioned conditions. The variety has been found to be suitable for climactic conditions in USDA Plant Hardiness Zone 8. Based on the performance of its recent ancestors, it is likely, although untested, that the new variety is also suitable for climatic conditions of USDA Plant Hardiness Zone 9.

*Drought tolerance*.—The new variety exhibits average drought tolerance.

I claim:

1. A new and distinct variety of shrub rose plant named 'Wicked Sister' characterized by the following combination of characteristics:

(a) abundantly, and continuously forms large clusters of pink colored blooms in the form of full-petalled rosettes, (b) exhibits an upright and arching growth habit, (c) exhibits exceptional heat tolerance, (d) forms disease resistant foliage with a smooth and slightly waxy finish, (e) is well suited for growing as a heat tolerant and carefree specimen, and as a source of attractive ornamentation and fragrance in the landscape.

substantially as illustrated and described herein.

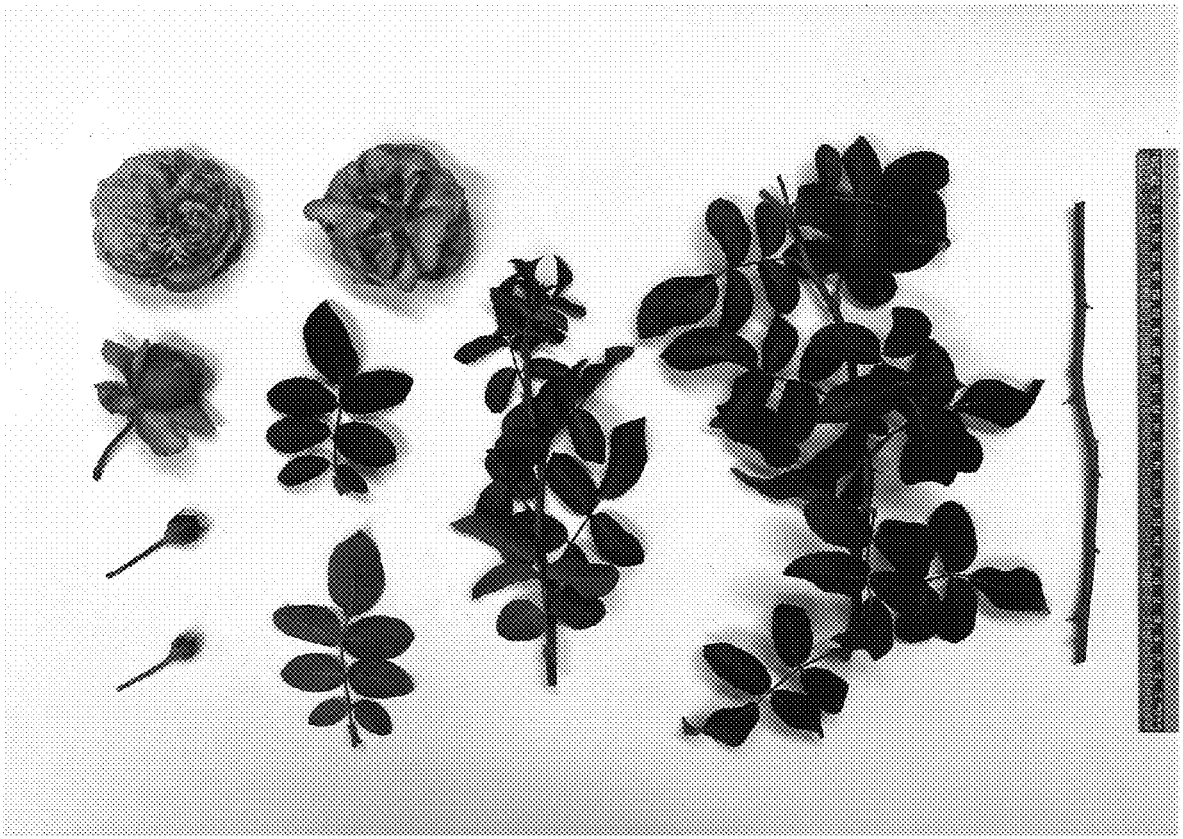

* * * * *